United States Patent [19]

Montgomery et al.

[11] Patent Number: 4,576,166

[45] Date of Patent: Mar. 18, 1986

[54] SURGICAL LIGATING INSTRUMENT

[75] Inventors: John R. Montgomery, Fairfield; Milton W. Brumaghim, Newton; Jose C. Deniega, Brookfield, all of Conn.

[73] Assignee: American Cyanamid Company, Stamford, Conn.

[21] Appl. No.: 278,258

[22] Filed: Jun. 29, 1981

[51] Int. Cl.⁴ .............................................. A61B 17/12
[52] U.S. Cl. ................................. 128/325; 29/243.56; 72/410
[58] Field of Search .................... 128/325, 334 R, 326; 227/DIG. 1; 29/243.56; 72/410

[56] References Cited

U.S. PATENT DOCUMENTS

| | | | |
|---|---|---|---|
| 3,837,555 | 9/1974 | Green | 227/130 |
| 4,242,902 | 1/1981 | Green | 128/325 |
| 4,246,903 | 1/1981 | Larkin | 128/325 |
| 4,299,224 | 11/1981 | Noiles | 128/325 |
| 4,316,468 | 2/1982 | Klieman et al. | 128/325 |
| 4,325,376 | 4/1982 | Klieman et al. | 128/325 |

FOREIGN PATENT DOCUMENTS 2074030 10/1981 United Kingdom ............... 128/325

Primary Examiner—Michael H. Thaler
Attorney, Agent, or Firm—Charles F. Costello, Jr.

[57] ABSTRACT

An improved surgical ligating instrument has been invented. The improvements comprise a crimping mechanism having canted jaws and an advancing mechanism having a clip actuator, said actuator having a first and a second pawl in alternate relationship.

A surgical ligating instrument has also been invented. The instrument comprises a. a housing having a force activating and translating mechanism; b. a loading mechanism having an injector, the terminal end adjacent a single clip; c. an advancing mechanism having a pair of aligned members, the initial end of the members contained in the housing and the terminal end containing jaws; a clip actuator rotatably mounted adjacent the initial end of the jaws; a spring, a pusher at the terminal end of the spring, and a plurality of clips, the rearmost clip adjacent the pusher and the frontmost clip contained by the actuator; and d. a crimping mechanism having a crimp bar.

5 Claims, 17 Drawing Figures

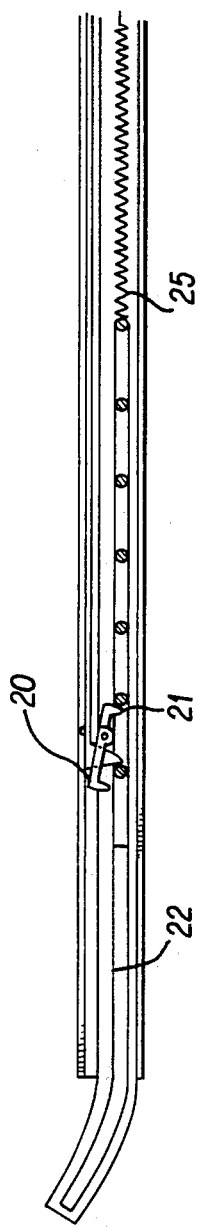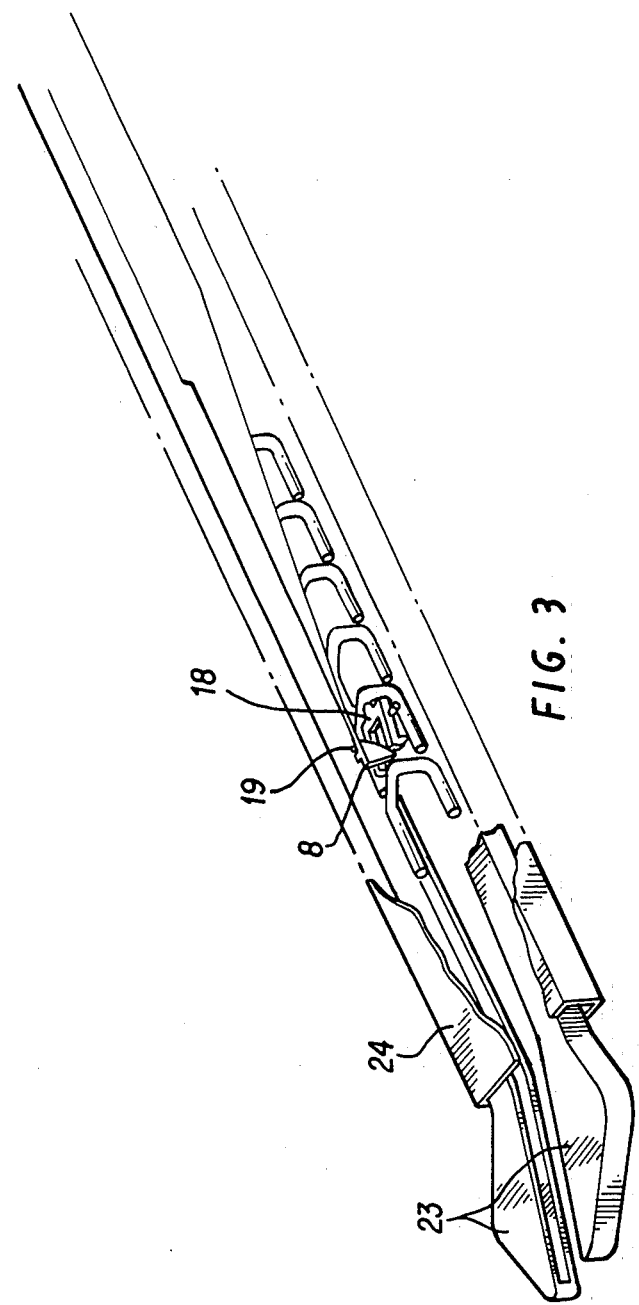

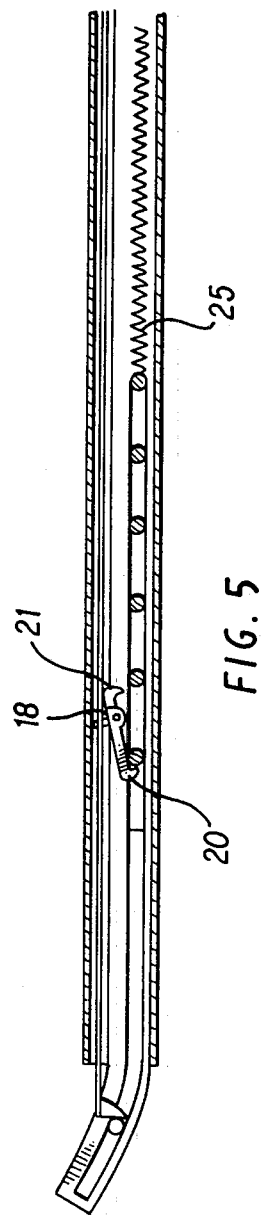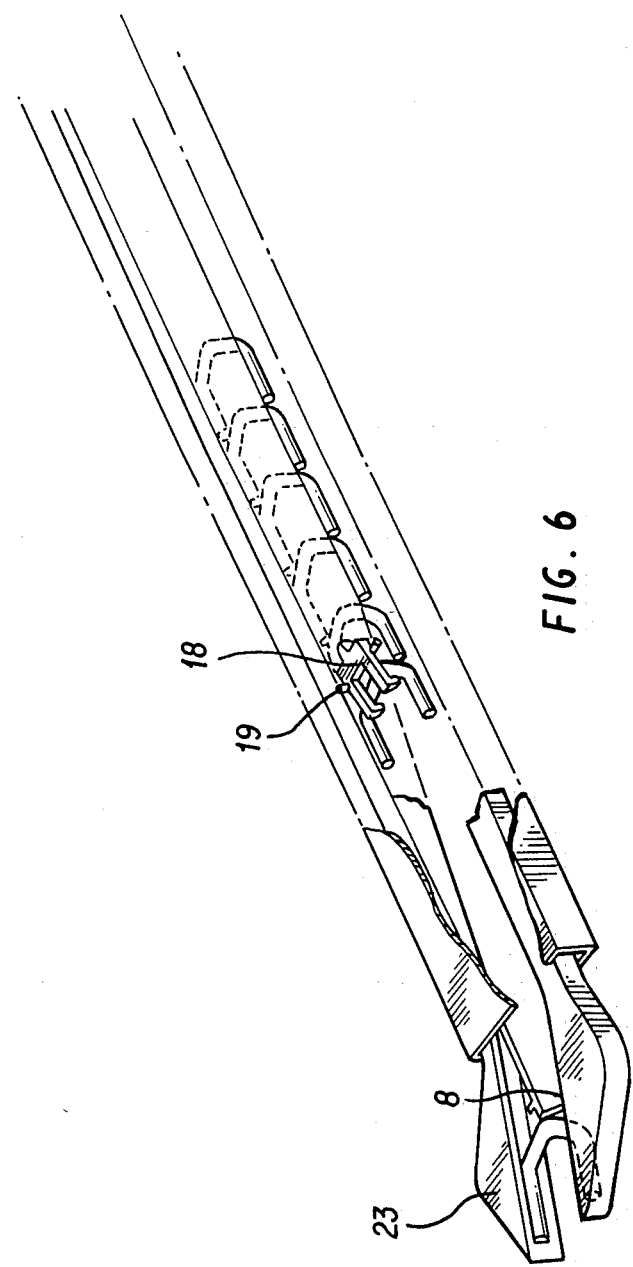

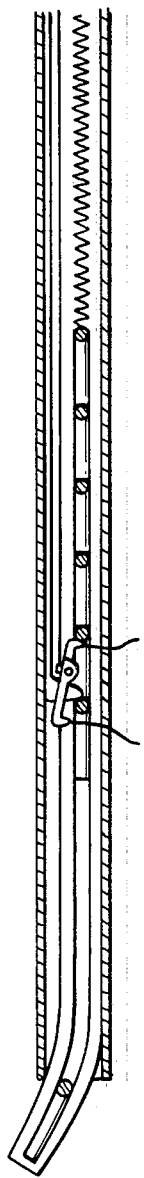
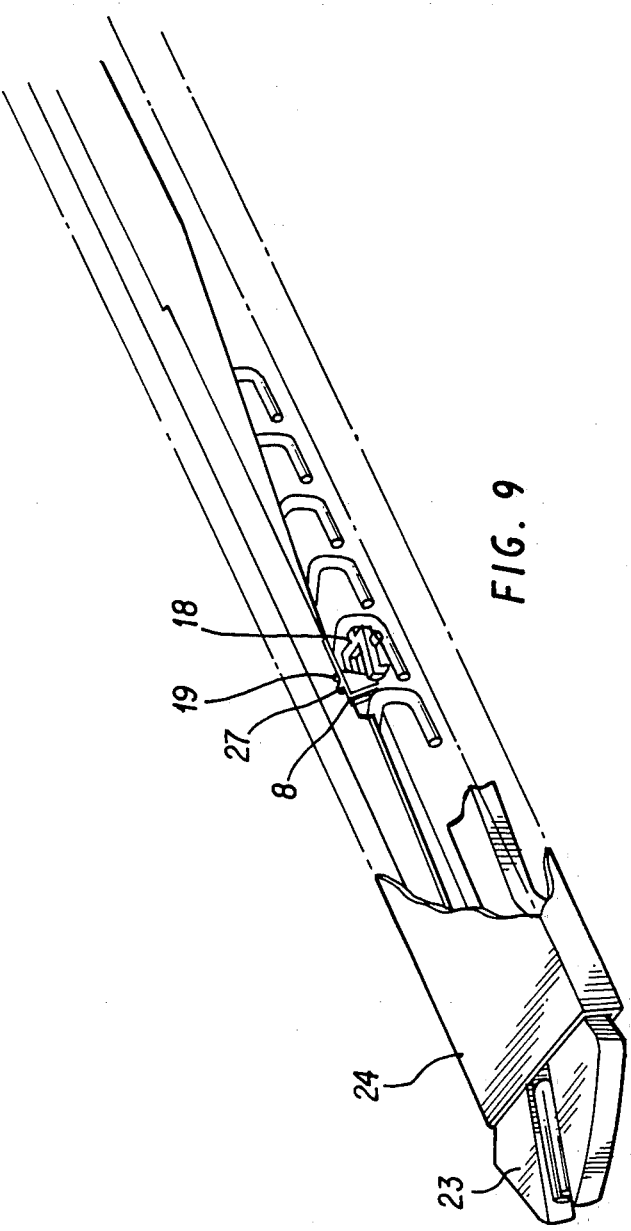

4,576,166

SURGICAL LIGATING INSTRUMENT

BACKGROUND AND SUMMARY OF THE INVENTION

This invention relates to an improved surgical ligating instrument having canted jaws. This invention also relates to a surgical ligating instrument having a plurality of ligating clips.

A surgical ligating instrument of this invention has advantages over the known prior art. One advantage is no rectilinear motion of the jaws during crimping. The accuracy of placing the ligating clip is thus improved or may even be maximized.

Another advantage is that the instrument can be operated "on site" with only one hand. The loading, advancing and crimping of the ligating clip(s) in the instrument is only with compression forces of the hand. The efficiency and time for ligating is thus greatly improved and may even be maximized.

Still another advantage are the canted jaws. In the instrument's relaxed position, a narrow gap separates the jaws. The clip opens the jaws during loading. The jaws will thus hold the clip prior to and during a partial crimping. That is, the clip remains in the jaws if the compression force on the jaws is released before complete crimping.

Yet another advantage is an integral clip loading (into the jaws) and advancing means. An integral system can improve the reliability of the instrument because the number of mechanical parts is reduced. Also, an integral system can decrease or even eliminate the possibility of double loading a clip into the jaws. Still yet another advantage is a clip injector having holding means. The injector can be held adjacent to a single clip in the jaws. The injector thus prevents the clip from backing out of the jaws prior to crimping. Also, the possibility of feeding another clip (double feeding) into the jaws is eliminated. Finally, because the trigger is depressed when the injector is adjacent a single clip in the jaws, the user has visual confirmation that the injector holding means has been activated.

Yet another advantage is a trigger lock which is activated when the instrument is exhausted of clips. The user thus has manual identification that there are no clips remaining in the instrument.

An improved surgical ligating instrument having loading, clip advancing and crimping means has been invented. The improvement comprises said crimping means having canted jaws whereby an uncrimped or a partially crimped clip can be maintained in said jaws. Another embodiment of the improved instrument is wherein said loading means load a ligating clip from the initial end of said jaws.

An alternative (or in combination with the above described improved instrument) surgical ligating instrument having loading means containing a single clip; advancing means containing a plurality of clips; and crimping means has been invented. The improvement comprises said advancing means having a clip actuator, said actuator having a first and a second pawl in alternate relationship whereby said actuator can repeatedly release the frontmost clip of said plurality of clips.

A surgical ligating instrument has also been invented. The instrument comprises a. a housing having a first and a second force activating and force translating means to effect a first and a second force, respectively.
b. loading means having an injector, the initial end of said injector adjacent said first translating means and the terminal end adjacent a single clip;
c. advancing means having a pair of aligned members, each member containing an external and an internal slot, the initial end of said members contained in said housing and the terminal end containing jaws; a clip actuator rotatably mounted adjacent the initial end of said jaws, said actuator having a first and a second pawl in alternate relationship; a spring, the initial end contained in said housing, a pusher at the terminal end of said spring, and a plurality of clips, the rearmost clip adjacent said pusher and the frontmost clip contained by said actuator, said spring, pusher and clips contained by the internal slots of said members, and said injector adjoining the external slots; and
d. crimping means having a crimp bar, the initial end adjacent said second translating means and the terminal end adjacent said jaws, said crimp bar holding said injector on said external slots.

Other embodiments of the above described surgical ligating instrument are wherein said first activating means is a trigger; and wherein said trigger is activated by at least one thumb.

Yet other embodiments of the above described ligating instrument are wherein said first translating means is a sector gear on the terminal end of said trigger and a rack on the initial end of said injector; wherein said first translating means has at least one reduction gear such that said sector gear meshes with said reduction gear, and said reduction gear meshes with said rack; wherein said injector has holding means, said holding means comprising a pin on the initial end of said injector and a rotatable pawl contained in said housing, the distance between said pin and rotatable pawl about equal to the travel of a single clip adjacent the terminal end of said injector to said jaws whereby said injector is held adjacent to said single clip in said jaws; and wherein said second activating means on complete compression rotates said rotatable pawl such that said pin can be released.

Still other embodiments of the above described instrument are wherein said injector contains a flanged portion and said pusher contains an opening whereby said flanged portion is held by said opening after said rearmost clip is crimped by said jaws; and wherein said first activating means is simultaneously locked as said flanged portion is held by said opening. The configuration of the opening is not critical provided the flanged portion can be held by the opening. A rectangular, square or circular opening can be used.

Still yet other embodiments are wherein said second activating means is a handle; wherein said handle is activated by at least one finger; and wherein said second translating means is a pin at the initial end of said crimp bar and a cam on said handle.

Still another embodiment is wherein said jaws are canted.

DESCRIPTION OF THE DRAWINGS

FIGS. 2 and 3 are cut-away bottom and partially broken perspective views of FIG. 1 showing the loading, clip advancing and crimping means;

FIGS. 5 and 6 are cut-away bottom and partially broken perspective views of FIG. 4 showing the position of the injector, jaws and clip actuator;

FIGS. 8 and 9 are cut-away bottom and partially broken perspective views of FIG. 7 showing the loading, clip advancing and crimping means.

DESCRIPTION OF THE PREFERRED EMBODIMENT

Figure 1:
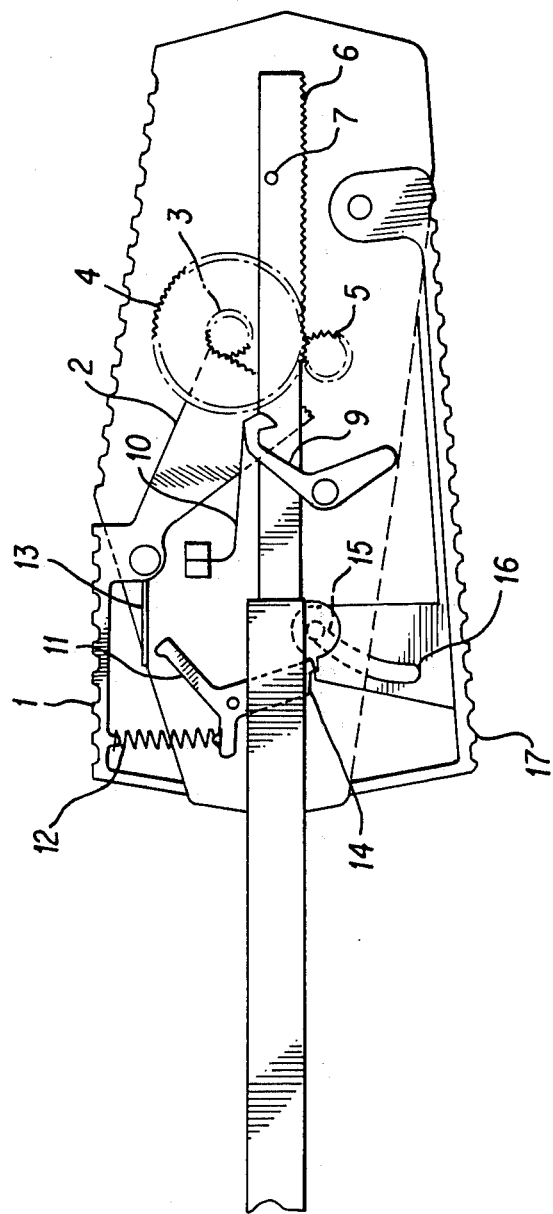
FIG. 1 is a broken cut-away side view of the instrument housing showing the activating and translating means in a rest position.

FIG. 1 shows the parts in the housing of the device. FIG. 2 is a cross-section and FIG. 3 is a schematic showing the parts in the probe. Referring to FIGS. 1 to 3, clip injector 8 is rigidly attached to rack 6. Alternatively, injector 8 can be manufactured as one part with the rack 6 contained on the initial end. Rack 6 carries pin 7.

Reduction gears 3 and 4 are keyed together to form a cluster. Alternatively, gears 3 and 4 can be manufactured as one part. Sector gear 2 meshes with gear 3, and gear 4 meshes with pinion gear 5. Rack 6 meshes with gear 5.

Spring 25 is compressed between a pusher and rack 6. The rearmost clip of a column of clips is adjacent the pusher. The spring is thus applying a constant force to urge a plurality of clips forward and the rack 6 backward.

A plurality of clips are contained in an internal slot that runs throughout the length of a pair of aligned members 23. The terminal end of the members 23 contain jaws.

Pin 15 is contained on and therefore is carried by the motion of crimp bar 24. The pin 15 rides on cam surface 16.

Figure 4:
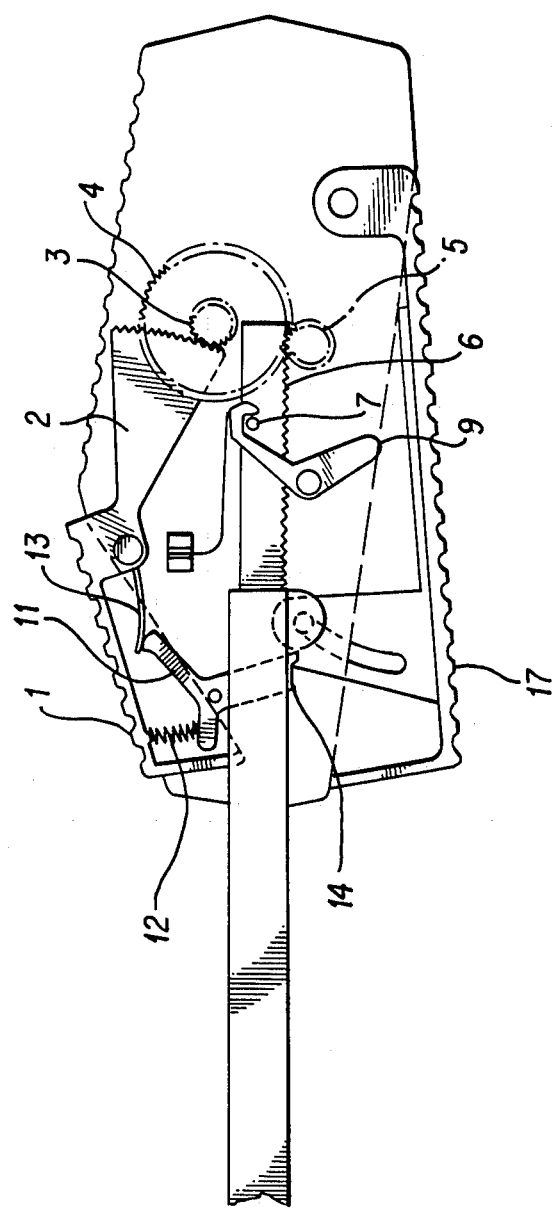
FIG. 4 is a broken cut-away side view of the instrument housing showing the first activating and translating means in the compressed position.

Referring to FIGS. 4 to 6, a single clip is pushed to the jaws by the clip injector 8. This is accomplished by compressing feed trigger 1 which turns sector gear 2 counter-clockwise and cluster gears 3 and 4 clockwise. Pinion gear 5 turns counter-clockwise driving rack 6 and clip injector 8 forward against spring 25, pushing the lead clip to the tip of the jaws (as shown in FIGS. 5 and 6). The clip injector 8 is held in the forward position by a rotatable pawl 9 which is contained in the housing and which catches pin 7.

Near the end of the forward stroke of the clip injector 8, a detent 8a (shown in FIG. 3) on the clip injector pushes the actuator stem 19 causing the actuator 18 to rotate forward dropping pawl 20 and lifting pawl 21. Since the column of clips is constantly being urged forward by spring 25, the clips which were being held back by pawl 21 (as shown e.g. in FIG. 2) are now free to slide forward until the lead clip is stopped by pawl 20.

Figure 7:
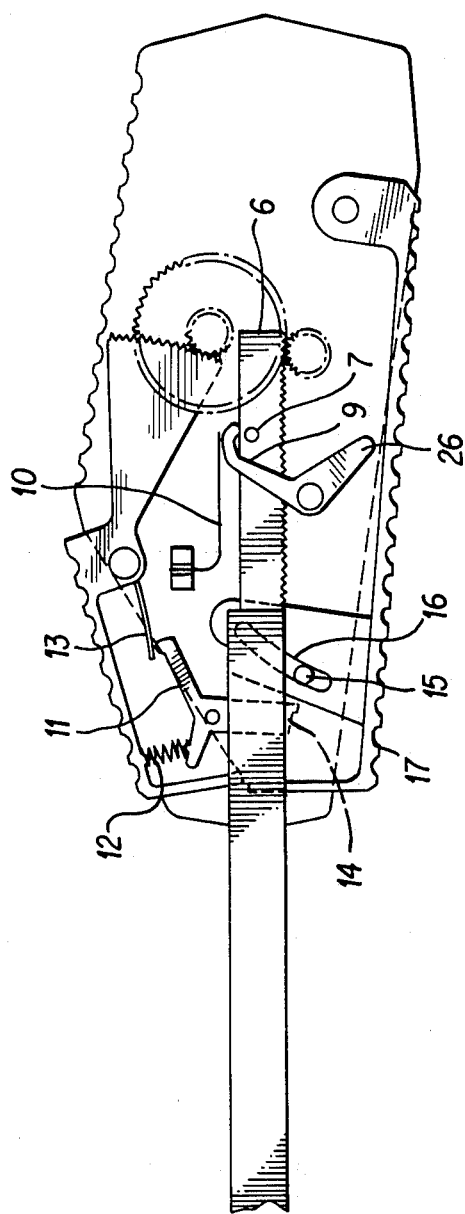
FIG. 7 is a broken cut-away side view of the instrument housing showing the second activating and translating means in the compressed position.

Referring to FIGS. 4 and 7 crimp bar interlock 11 prevents the handle 17 from being depressed until trigger 1 is completely compressed. Compression spring 12 applies a constant force to urge a first lever arm 11a to turn counter-clockwise. When the trigger 1 is approximately one-half compressed, leaf spring 13 will hit a second lever arm 11b. Because the force of leaf spring 13 is greater than spring 12 and because the effective length of the second lever arm is longer than the first lever arm, leaf spring 13 overides compression spring 12. Therefore, crimp bar interlock 11 tends to turn clockwise.

If there is pressure on the crimp bar handle 17 when trigger 1 is depressed, dog 14 does not disengage. Crimp bar handle 17 is thus prevented from being compressed. When the pressure on the crimp bar handle 17 is released, dog 14 disengages. This action causes crimp bar interlock 11 to turn clockwise. The cam plate 16 carried by the crimp bar handle 17 is thus activated.

The clip which has been in the jaws is now ready to be crimped. This is accomplished by completely compressing the crimp bar handle 17.

Referring specifically to FIGS. 7 to 9, as the crimp bar handle 17 is being compressed, crimp bar 24 is pushed forward by the pin 15 acting on cam 16. The front end of the crimp bar 24 cams on the incline planes at the jaws 23. The camming causes the two jaws to come together crimping the clip.

As the crimp bar handle 17 approaches a complete compression, it contacts lever 26 pushing pawl 9 up against leaf spring 10 and releasing pin 7. The rack 6 is now free to slide back pulling with it the injector 8. As shown in FIG. 9, tab 27 hits stem 19, rotating clip actuator 18. This drops pawl 21 to hold back the column of clips that is being urged forward by spring 25, and lifts pawl 20 to clear the path for the lead clip. The front end of the clip injector 8 is flexible such that it cams over and gets behind the lead clip. The injector 8 can contain a flanged portion at the terminal end and the pusher can contain an opening such that the flanged portion is held by the opening after the rearmost clip is crimped by the jaws. The trigger 1 is thus locked when the clips are exhausted.

In the relaxed position, a narrow gap separates the jaws 23. The clip opens the jaws during loading. The jaws can thus hold the clip before crimping, and also during partial crimping, that is, if the crimp bar handle 17 is released before complete compression.

Referring to FIGS. 11 and 14 to 16, the surgical ligating instrument has a housing 30. The housing contains a first activating means, for example a trigger 1, and a second activating means, for example a handle 17. The first and second force translating means is activated by the trigger 1 and the handle 17, respectively.

Figure 10:
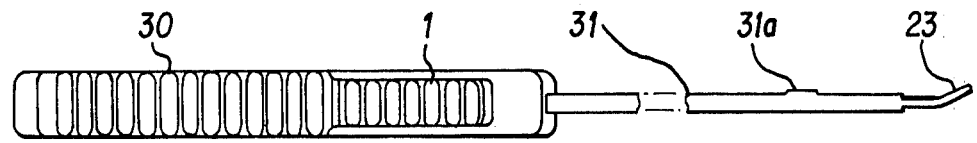
FIG. 10 is a partially broken top plan view of a surgical ligating instrument showing our new design.
Figure 11:
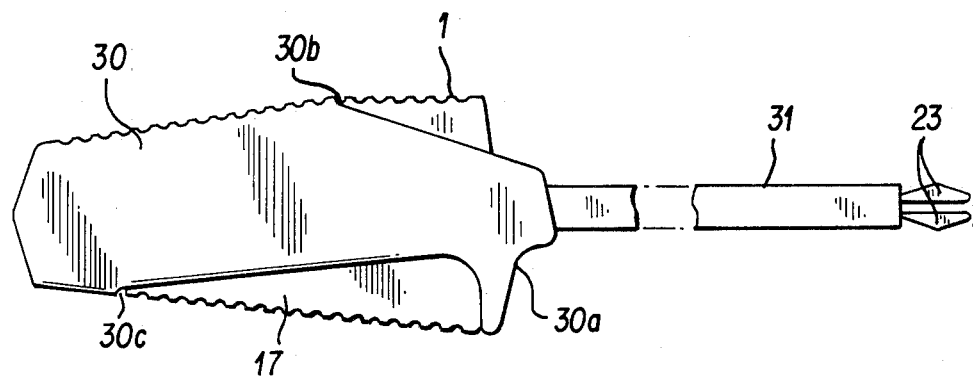
FIG. 11 is a partially broken side elevation of FIG. 1.
Figure 17:
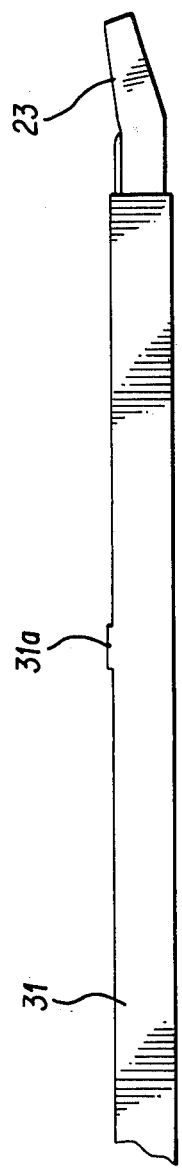
FIG. 17 is a broken and exploded top plan view showing the probe of FIG. 1.

Referring to FIGS. 10, 11 and 17, the instrument has a probe 31. The initial end of the loading, advancing and crimping means is contained in the housing 30.

The housing 30 is in substantial parallel alignment with the probe 31. Preferably, the first activating means 1 and the upper portion of the housing are in a diagonal alignment with the probe 31. A diagonal alignment seems to counteract the optical and manual illusion that the probe is nonparallel with the housing and may better conform to the contour of the hand.

Preferably, the size of the housing is such that a predominant portion of the housing can be essentially held by the palm of a hand.

The terminal end of the probe 31 contains jaws 23.

Referring to FIG. 11, in one embodiment the housing has a curved portion 30a between the second activating means 17 and the probe 31. An index finger can be placed on the curved portion.

Figure 14:
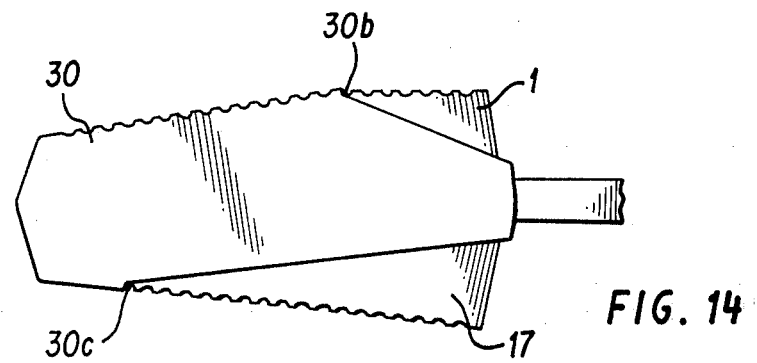
FIGS. 14 to 16 are alternative side elevation views of a surgical ligating instrument of FIG. 2.
Figure 15:
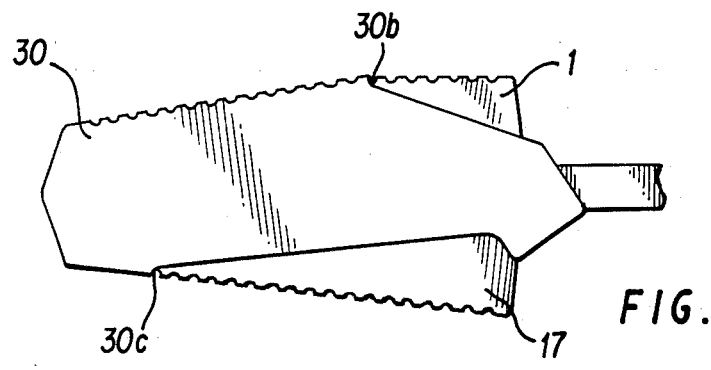
Figure 16:
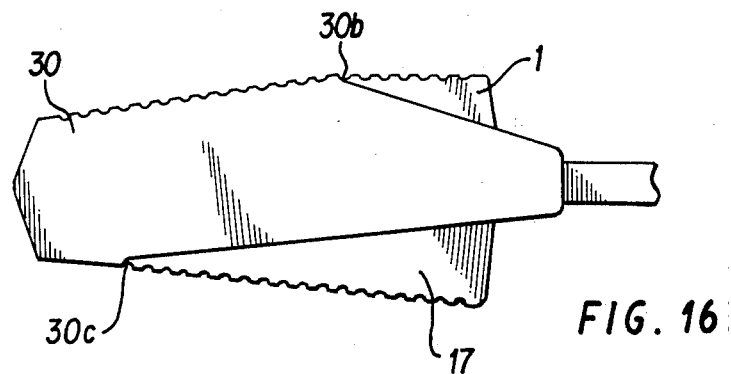

FIGS. 14 to 16 are alternative embodiments of the surgical instrument housing shown in FIGS. 10 to 13. The description of the housing of FIGS. 10 to 13 essentially corresponds to FIGS. 14 to 16.

FIG. 17 describes in more detail the probe 31. The optional raised portion 31a can be a transparent material and is adjacent to the initial end (not shown) of the jaws 23 in the probe. The raised portion gives a visual identification to the user that clips are/are not remaining in the instrument.

Figure 12:
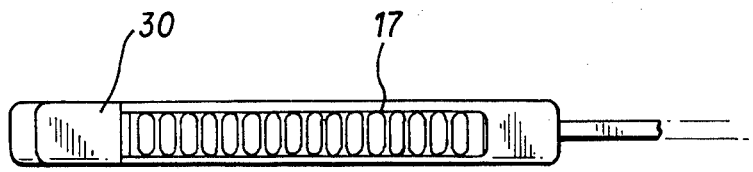
FIG. 12 is a back plan view of FIG. 2.
Figure 13:
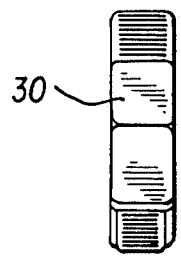
FIG. 13 is a back plan view of FIG. 2.

Referring to FIGS. 10 to 15 a scalloped configuration in the upper portion of the housing and the first activating means and in the lower portion of the second activating means is preferred. The scalloping assists the user to grip the housing and to compress the first and the second activating means. The partial and broken scalloping shown in FIGS. 10 to 12 are for clarity of illustration. It is to be understood that the scalloping in FIGS. 10 and 12 is consistent with FIG. 11. It is also to be understood that the probe shown in FIG. 11 is identical in FIGS. 14 to 16.

A notch 30b between the first activating means and the upper portion of the housing, and a notch 30c between the second activating means and the lower portion of the housing reduces or may even eliminate the possibility that the hand and/or fingers of the user are punched when the first and the second activating means are returning to the relaxed position.

We claim:

1. A surgical ligating instrument comprising
A. a housing having
  I. a trigger, which can be activated by at least one thumb to cause a first force;
  II. a sector gear on the distal end of said trigger, at least one reduction gear which meshes with said sector gear, and a rack which meshes with said reduction gear, to effect said first force;
  III. a handle, which can be activated by at least one finger to cause a second force;
  IV. means for translating said second force from said handle to a movable pin, to effect said second force; and
  V. an interlock between said trigger and said handle such that said trigger is completely compressed before said handle is compressible; and
B. a probe having
  I. means for advancing a plurality of ligating clips comprising
    a. a pair of aligned members, each member containing an internal slot, the proximal end of said members contained in said housing and the distal end having canted jaws, said jaws during compression of said handle having no rectilinear motion relative to said housing;
    b. a single clip actuator rotatably mounted adjacent the proximal end of said jaws, said actuator having a first and a second pawl in alternate relationship such that said actuator can repeatedly release the frontmost clip from said plurality of clips;
    c. a spring, the proximal end contained to said housing;
    d. a pusher at the distal end of said spring; and
    e. a plurality of clips, the rearmost clip adjacent said pusher and the frontmost clip contained by said actuator, said spring, pusher and clips contained by the internal slots of said aligned members;
  II. means for loading a ligating clip from the proximal end of said jaws comprising an injector, said injector having holding means such that said injector can be held adjacent to a single clip in said jaws, the proximal end of said injector adjacent said rack in said housing and the distal end adjacent a single clip, said injector adjoining said aligned members; and
  III. means for crimping a single clip in said jaws comprising a movable crimp bar, the proximal end adjacent said movable pin in said housing and the distal end adjacent said jaws.

2. An instrument of claim 1 wherein said holding means comprises a pin on the initial end of said injector and a rotatable pawl contained in said housing, the distance between said pin and rotatable pawl about equal to the travel of a single clip adjacent the terminal end of said injector to said jaws.

3. An instrument of claim 2 wherein said second activating means on complete compression disengages said rotatable pawl such that said pin can be released.

4. An instrument of claim 1 wherein said injector contains a flanged portion and said pusher contains an opening whereby said flanged portion is held by said opening after said rearmost clip is crimped by said jaws.

5. An instrument of claim 4 wherein said first activating means is simultaneously locked as said flanged portion is held by said opening.

* * * * *